United States Patent [19]
Klein

[11] 3,945,597
[45] Mar. 23, 1976

[54] MICROSURGICAL OPERATING UNIT

[75] Inventor: Friedrich Klein, Wedel, Holstein, Germany

[73] Assignee: J. D. Möller Optische Werke GmbH, Wedel, Holstein, Germany

[22] Filed: Feb. 11, 1974

[21] Appl. No.: 441,450

[30] Foreign Application Priority Data
Mar. 7, 1973 Germany............................ 2311257

[52] U.S. Cl. .............................................. 248/327
[51] Int. Cl.² ........................................ F16M 13/00
[58] Field of Search .......... 248/280, 281, 324, 325, 248/327

[56] References Cited
UNITED STATES PATENTS

| | | | |
|---|---|---|---|
| 2,076,446 | 4/1937 | Carwardine.......................... | 248/280 |
| 2,301,661 | 11/1942 | Wiedenhoeft................ | 248/281 UX |
| 2,665,102 | 1/1954 | Perbal................................. | 248/280 |
| 2,734,710 | 2/1956 | Noble ............................. | 248/281 X |
| 2,837,307 | 6/1958 | Schwager et al..................... | 248/325 |
| 2,919,098 | 12/1959 | Mull et al. ....................... | 248/327 X |
| 3,409,261 | 11/1968 | Leporati ............................. | 248/281 |
| 3,615,067 | 10/1971 | Goudreau ............................ | 248/325 |

Primary Examiner—William H. Schultz
Attorney, Agent, or Firm—Toren, McGeady and Stanger

[57] ABSTRACT

A microsurgical operating unit for the movable installation of an operating microscope in an operating theater. The unit includes a ceiling member for attachment to the ceiling, several pivotably interconnected members for holding and locking the microscope in any desired orientation, and a motor drive for elevation adjustments of the microscope.

8 Claims, 10 Drawing Figures

MICROSURGICAL OPERATING UNIT

The present invention relates to a microsurgical operating unit adapted to be installed at the ceiling of an operating theater and serving to mount and control an operation microscope.

Heretofore known mountings for operation microscopes include telescopically adjustable tubular elements for the purpose of height adjustment of the microscope, and either crank-type twin arms or guide rails for lateral adjustment, i.e., adjustment of the microscrope in a desired vertical plane. These known microsurgical operating units may be used efficiently if the operating field is relatively small and preferably confined to a limited area, as is usually the case in ophthalmological and otological applications.

For adjustment of the microscope within a more extended space the known microsurgical operating units, however, are less suitable because telescopic assemblies require for long extensions a correspondingly increased overall length which in turn may lead to problems of installation in rooms with lower ceiling levels. Moreover, multi-segment telescopic tubes do not have the required rigidity, due to inevitable fit clearances. With twin arms and guide rails, on the other hand, the necessary insensitivity to vibrations cannot be obtained.

It is therefore the object of the present invention to provide a novel and improved microsurgical operating unit of a small vertical installation extension, having well placed, readily accessible control elements, and designed so as to ensure the required rigidity of the microscope suspension.

In accordance with the present invention there is now proposed a microsurgical operating unit that is characterized by a vertical support column mounted at its upper end at the ceiling of a room such as an operating theater, a sleeve rotatably supported on the vertical support column, a pivot arm for height adjustment, the pivot arm being rotatably mounted about a horizontal pivot axis disposed adjacent the free lower end of the sleeve, a vertical pendulum arm rotatably mounted at the free lower end of the pivot arm, and a microscope mounted at an articulation on the free lower end of the pendulum arm.

Furthermore, a pivot mounting for horizontal alignment of the microscope may be interposed between the articulation and a microscope mounting, and there may be provided a parallelogram-type control linkage, a chain drive or the like for maintaining the microscope in a vertical orientation in any rotational position of the pendulum arm.

In accordance with additional features of the present invention, for alignment of the microscope in a vertical position during rotation of the pendulum arm, a first sprocket and the microscope mounting are rigidly secured to the articulation axis on the free lower end of the pendulum arm, a second sprocket is operatively coupled by a chain to the first lower sprocket, the second sprocket is rigidly secured to a shaft, the shaft is rotatably journalled in the upper articulation and operatively couples the pivot arm to the pendulum arm, a lever is secured to a projecting portion of the shaft, a connecting rod is rotatably connected at its one end to the free end of the lever, and rotatably connected at its opposite end to a fixed pivot point on the sleeve rotatably mounted on the support column. This sleeve and the chain interconnecting the two sprockets form part of a parallelogram-type control linkage for the microscope.

To enhance the mobility, i.e., the ease of handling of the microscope, a mass balance is provided for the pendulum arm and the microscope.

For height adjustment of the microscope the pivot arm is coupled to a motor drive, and a control panel for controlling the motor drive is arranged on the microscope mounting.

In the following, the novel microsurgical operating unit according to the present invention will be described with reference to a preferred embodiment as shown in the appended drawings wherein.

Figure 1:
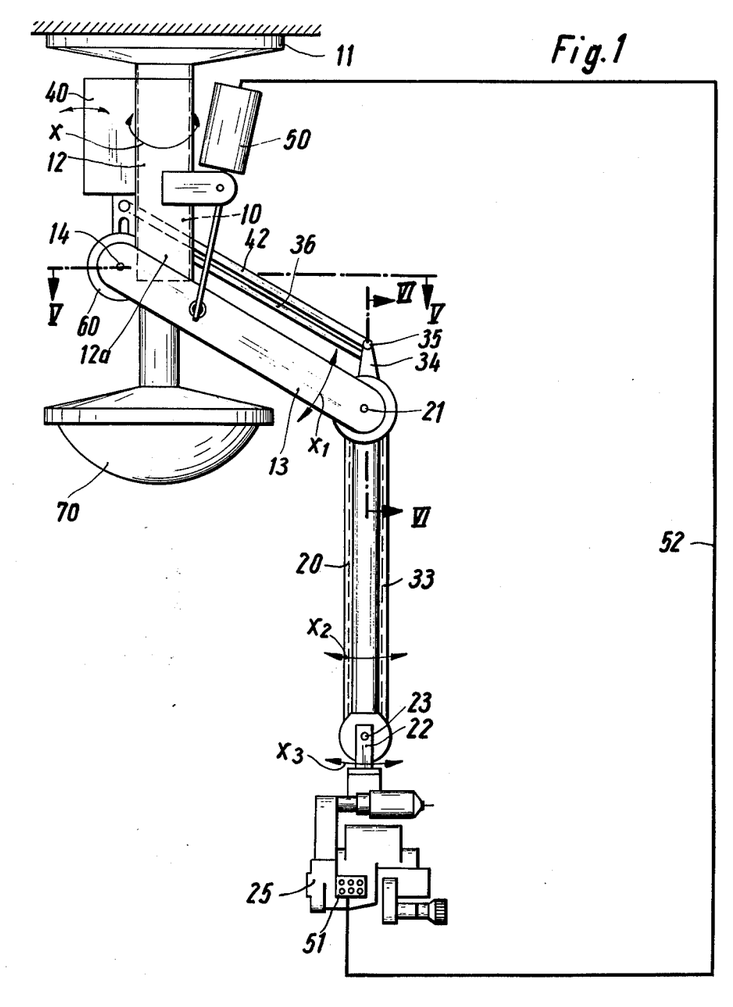
FIG. 1 is a front elevational view of a microsurgical operating unit according to the present invention.
Figure 2:
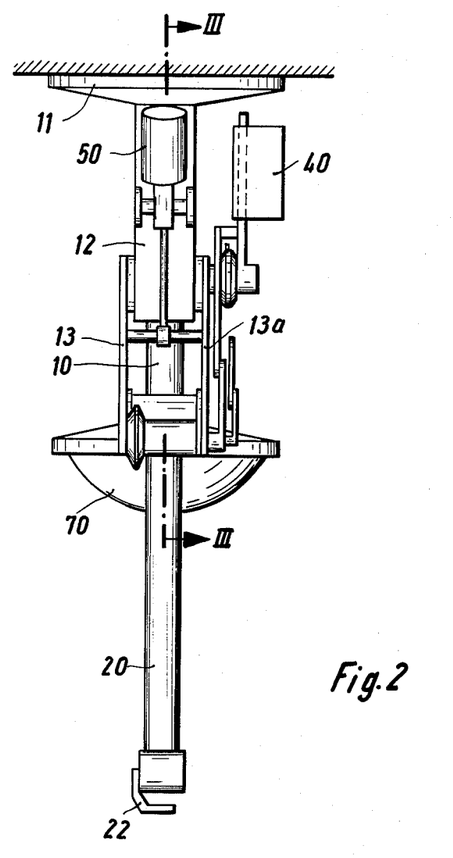
FIG. 2 is a lateral elevational view of the microsurgical operating unit of FIG. 1.
Figure 5:
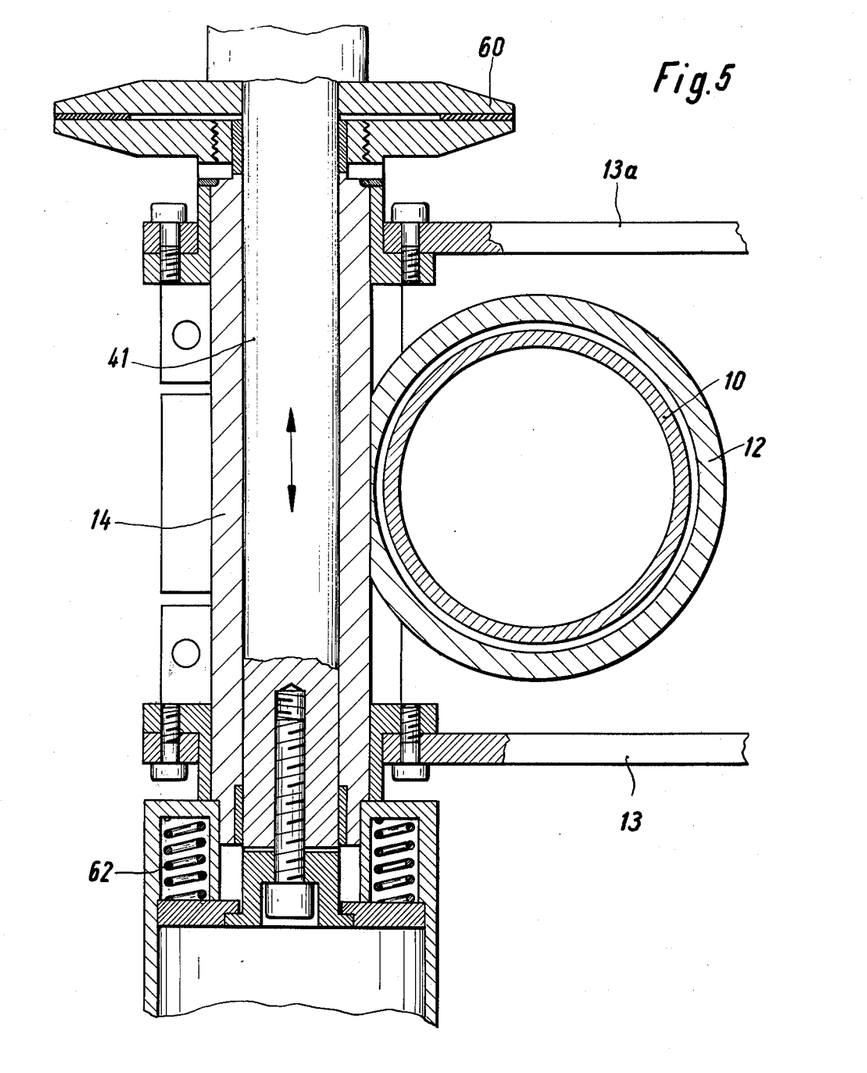
FIG. 5 is an enlarged horizontal cross-sectional view along the line V—V of FIG. 1.

Referring to FIGS. 1 and 2 of the drawings, the microsurgical operating unit includes a vertical support column 10 to which is rigidly secured at one end a mounting plate 11 that is fixed to the ceiling of a room such as an operating theater. A sleeve 12 is rotatably mounted on the support column 10, as may perhaps be seen best in FIG. 5. The lower end 12a of the sleeve 12 mounts a pivot arm 13 or a two-armed pivot arm consisting of a pair of flat-section pivot arm members parallel to each other, and indicated in FIG. 5 by the reference numerals 13 and 13a respectively. The pivot arm 13 or the pair of parallel disposed pivot arm members 13, 13a are rotatably mounted about a horizontal pivot axis 14 on the sleeve 12 so that the two pivot arm members 13, 13a may be oscillated in the direction of the double headed arrow $x_1$. The sleeve 12 may be rotated in the direction of the double headed arrow $x$.

A pendulum arm 20 is rotatably mounted at the free lower end of the pivot arm 13 or of the pivot arm members 13, 13a respectively. As shown in the drawings, the pendulum arm 20 is held in a vertical position and may be rotated about a horizontal axis 21 in the directions indicated by the double headed arrow $x_2$ (see FIGS. 1 and 2). A mounting 22 is rotatably mounted at the free lower end of the pendulum arm 20 and serves to attach a mircroscope 25 of a type known per se. The mounting 22 which is rotatably mounted on the pendulum arm 20 may be rotated about a horizontal axis 23 in the directions indicated by the double headed arrow $x_3$.

The pendulum arm 20 serves to adjust the microscope 25 into a desired horizontal position, whereas the pivot arm 13 serves to adjust the microscope 25 into any desired height within a given adjustment range. The pivot axis 14 of the pivot arm 13, the pivot axis 21 of the pendulum arm 20 and the pivot axis 23 of the microscope mounting 22 are spatially parallel to each other.

Figure 3:
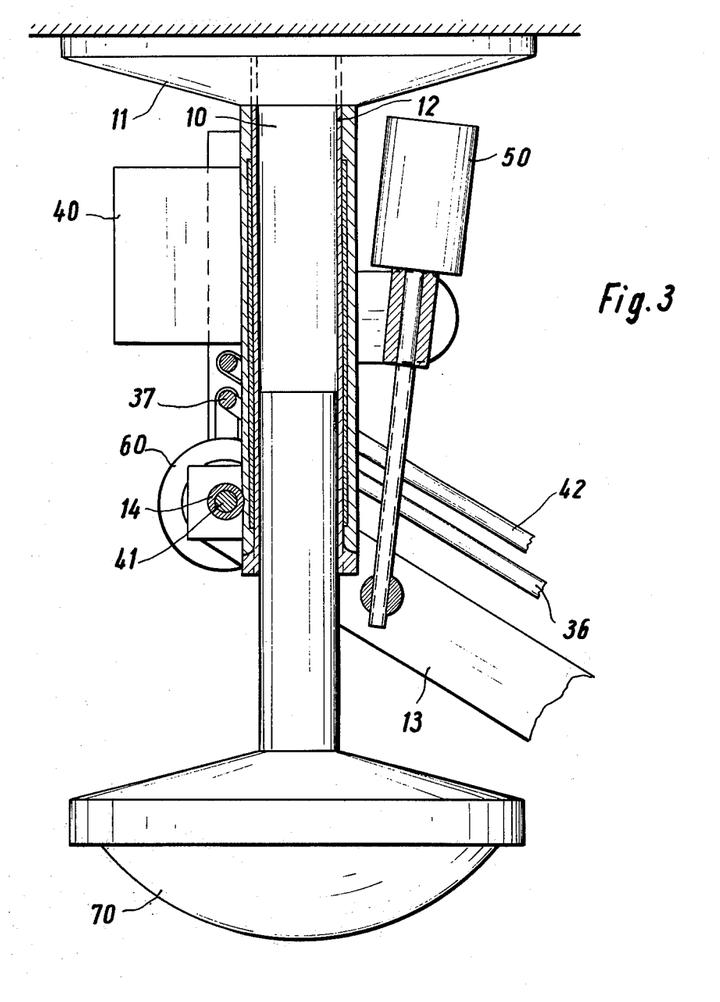
FIG. 3 is an enlarged cross-sectional vertical view along the line III—III of FIG. 2.
Figure 4:
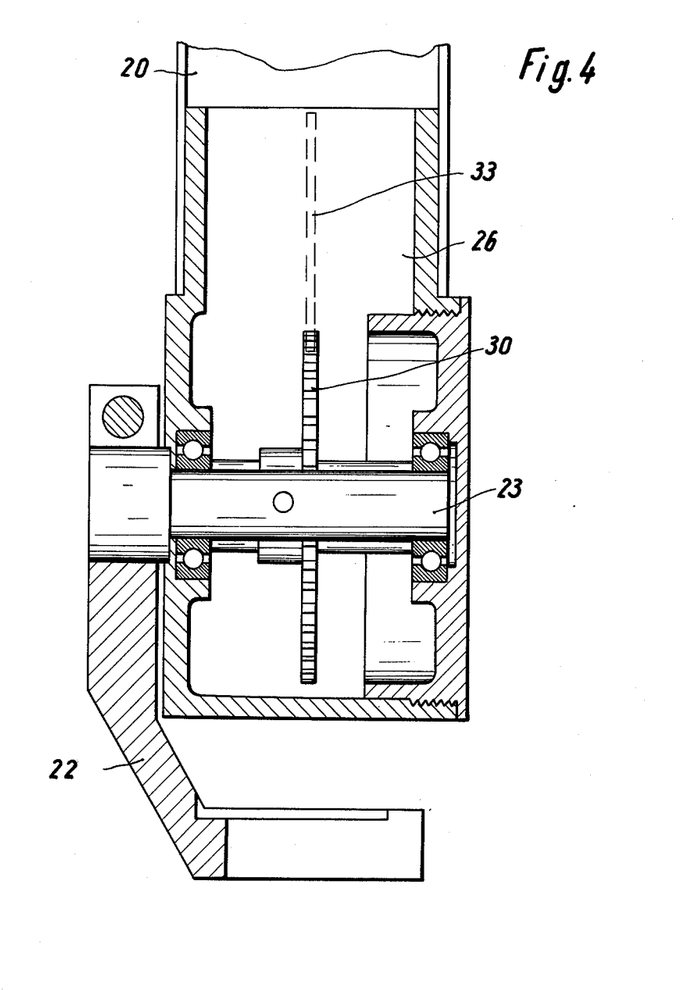
FIG. 4 is a fragmentary view of the mounting for the microscope, partly in elevation and partly in vertical cross-section.
Figure 6:
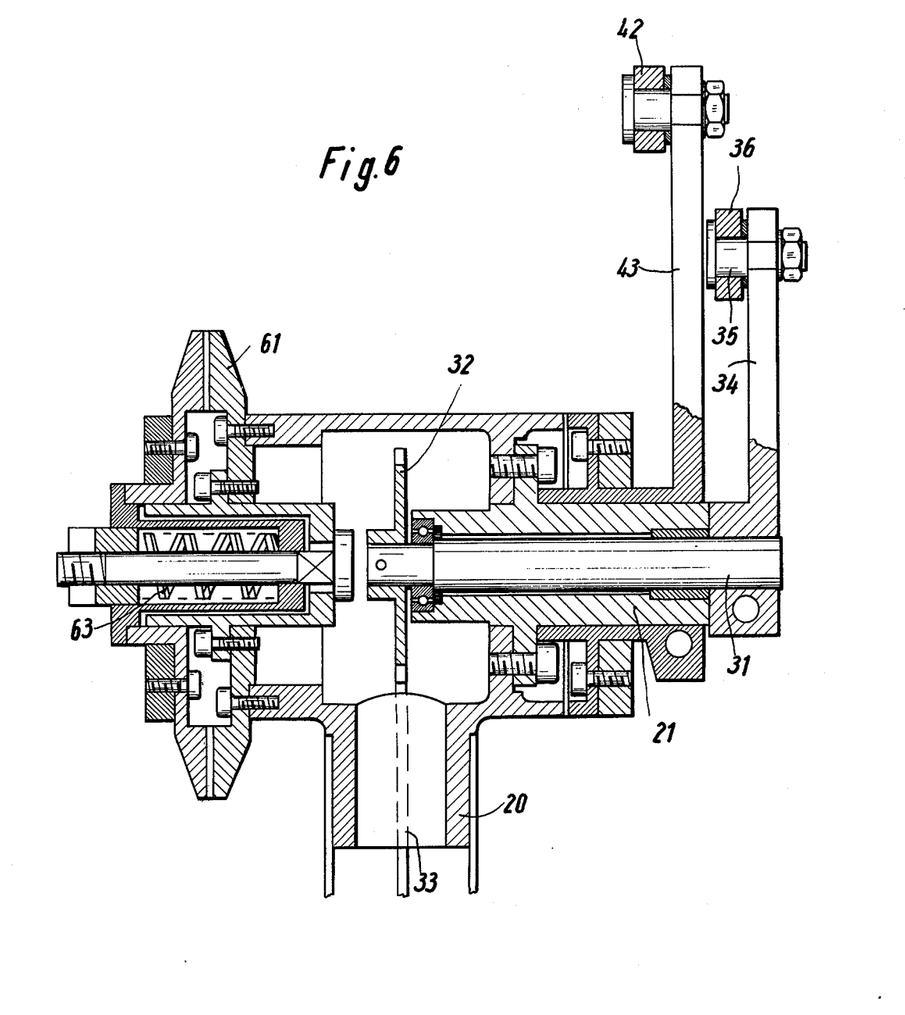
FIG. 6 is an enlarged vertical cross-sectional view along the line VI—VI of FIG. 1.

As an important feature of the present invention, the mounting 22 of the microscope 25 will always be maintained in a predetermined and preferably vertical alignment, independently of the positions assumed by the pivot arm 13 and the pendulum arm 20. This is achieved by suitable means such as a parallelogram-type control linkage, a chain drive or the like. In the embodiment shown in the drawings there is provided a chain drive for this purpose. To this end, the pendulum arm 20 is arranged in the form of a hollow cylindrical or tubular member defining a correspondingly shaped interior cavity 26. A sprocket 30 is mounted in the interior 26 of the pendulum arm 20 on the pivot axis 23 of the microscope mounting 22 (see FIG. 4). A shaft 31 is provided in the pivot axis 21 defining the articulation between pivot arm 13 and pendulum arm 20. A second sprocket 32 is mounted on the shaft 31 and operatively coupled by a chain 33 to the first sprocket 30 mounted in the lower end of the pendulum arm 20 opposite the microscope mounting. A lever 34 is fastened to a projecting end portion of the shaft 31 which shaft end portion is opposite to the shaft end portion bearing the sprocket 32. A connecting rod 36 is rotatably coupled at 35 to the free upper end of the lever 34. The other end of the connecting rod 36 is rotatably coupled at 37 to a pivot point at the sleeve 12 (see FIGS. 1, 3 and 6). The chain 33 which extends along the interior 26 of the pendulum arm 20, the lever 34 which is mounted on the shaft 31, and the connecting rod 36 jointly define the parallelogram-type control linkage holding the articulation 23 for the microscope mounting 22 in a desired orientation. The two strands of the chain 33 extend on opposite sides of the pendulum arm 20 within suitable pendulum arm guideways (not shown) or within a casing mounted externally on the pendulum arm 20.

For enhancing the mobility, i.e., the ease of handling of the microscope 25 a mass balance is provided for the pendulum arm 20 and the microscope 25 supported thereby. This mass balance may consist of a counterweight attached to an upper extension of the pendulum arm 20. Preferably, the weight 40 shown in FIGS. 1 and 2 is mounted at a smaller spacing from the horizontal pivot axis 14 of the pivot arm 13. This may be achieved, as shown in FIGS. 1 and 2, by mounting the weight 40 in the pivot axis 14 of the pivot arm 13 by means of a shaft 41 which — as may be seen best in FIG. 3 — is rotatably journalled within an internal bore of the pivot axis 14. The weight 40 is furthermore connected to the pendulum arm 20 by a parallelogram rod 42 and a lever 43 that is connected to the pivot axis 21 (see FIG. 6). This arrangement is highly advantageous, as will be explained further below.

Elevational movements of the microscope 25 may likewise be counterbalanced by means of a counterweight on the pivot arm 13. Preferably, however, there is provided a motor drive 50 for effecting up and down pivot movements of the pivot arm 13. For controlling the motor drive 50 there is provided a control panel 51 with suitable actuators on the microscope 25 itself or on the microscope mounting 22 (see FIGS. 1 - 3). The control cable 52 schematically shown in FIG. 1, by which the motor drive 50 is connected to the control panel 51, is of course installed along the interiors of the support column 10, the pivot arm 13 and the pendulum arm 20, so as not to interfere with the adjustment movements of the microscope 25.

The shaft 41 for the counterweight 40 in the pivot axis 14 and the articulation 21 of the pendulum arm 20 on the pivot arm 13 are each provided with a clamping device 60, 61 respectively. Each clamping device 60, 61 is continuously biased by suitably designed spring assemblies 62 and 63 respectively (see FIGS. 1, 5 and 6). When it is intended to adjust the microsurgical operating unit the clamping devices 60, 61 may be deactivated by means of hydraulic or pneumatic pistons, solenoids or the like not shown in the drawings.

Figure 7:
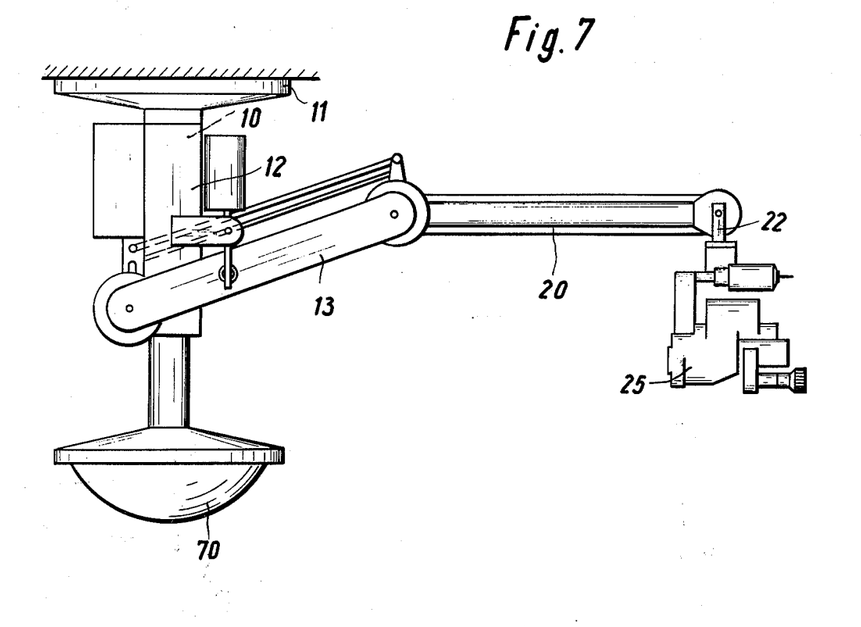
FIG. 7 is an elevational view of the microsurgical operating unit with the microscope moved into its uppermost position.
Figure 8:
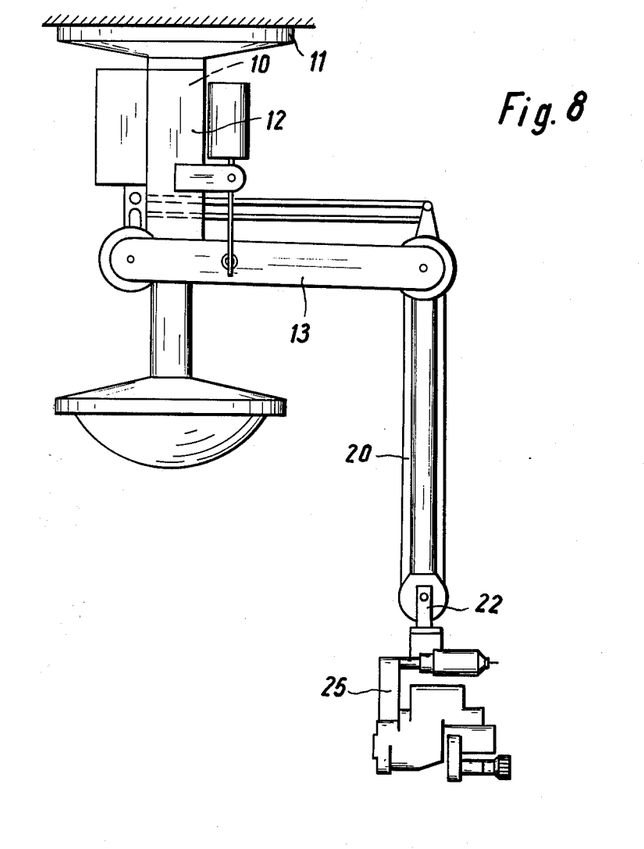
FIG. 8 is a view similar to FIG. 7, with the microscope moved into a position in which the pivot arm includes substantially a right angle with the pendulum arm.
Figure 9:
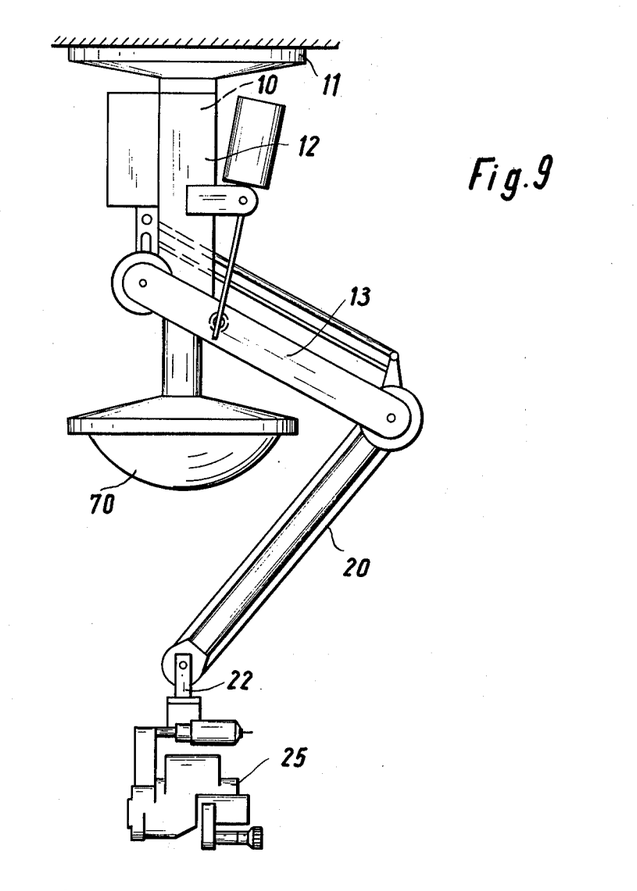
FIG. 9 is a view similar to FIG. 7 in which the microscope has been moved into a position below the vertical support column of the microsurgical operating unit.
Figure 10:
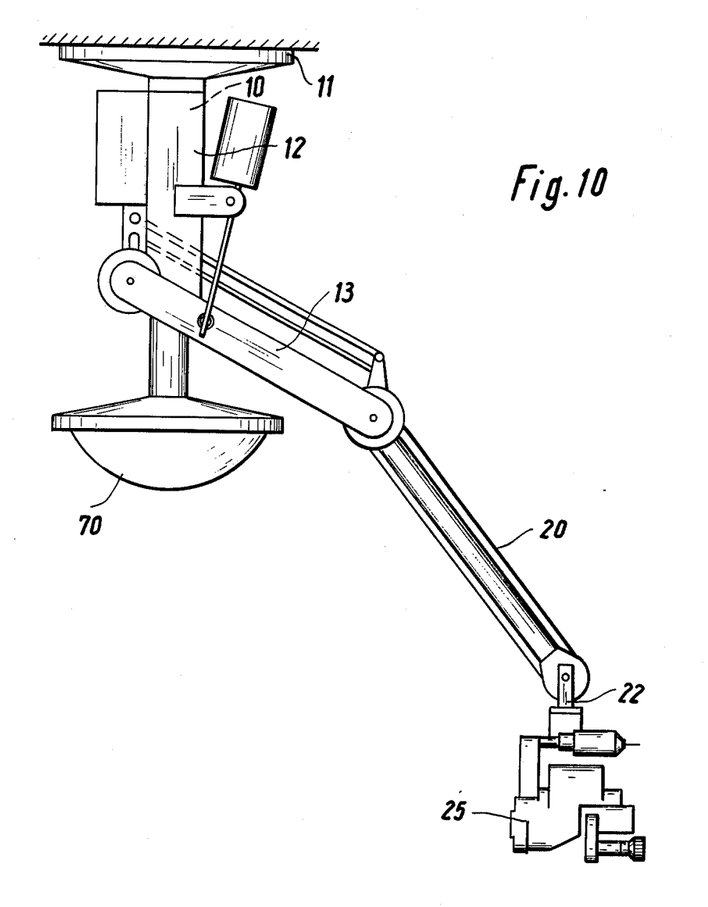
FIG. 10 is a view similar to FIG. 7 in which the pivot arm and the pendulum arm are aligned along a nearly straight line.

The microsurgical operating unit of the present invention allows the following methods of operation: When both clamping devices 60 and 61 are deactivated, the microscope 25 may be moved freely, both manually and by the motor drive 50. When deactivating the clamping device 60 for the counterweight 40, the microscope 25 may be rotated about the pivot axis of the counterweight into the inoperative or rest position shown in FIG. 7, or into any desired operative position. When deactivating the clamping device 61 in the pendulum arm articulation the pendulum arm 20 may be moved upwardly or downwardly, parallel to itself, by a rotational movement of the pivot arm 13. This movement allows minor height adjustments without defocussing the microscope 25.

FIGS. 7 - 10 show various rotational positions of the microscope 25.

The vertical support column 10 consists of a hollow cylindrical tube and is provided with an internal mounting for a vertically adjustable operating lamp 70. About the circumference of the lamp 70 may be provided various outlets for electrical power, compressed air, vacuum and the like, as well as control elements and switches for the lamp.

The novel microsurgical operating unit of the present invention needs only a very restricted space for its installation and allows a precise and steady adjustment of the microscope. The relatively small extension of the unit in vertical direction enables the operating surgeon free movements below the operating unit.

What is claimed is:

1. A microsurgical operating unit comprising a vertical support column mounted at its upper end to the ceiling of a room such as an operating theater, a sleeve rotatably supported on said vertical support column, a height-adjustment pivot arm rotatably mounted about a horizontal pivot axis disposed adjacent the lower free end of said sleeve, a vertical pendulum arm rotatably mounted at the free lower end of said pivot arm, a microscope mounted at an articulation on the free lower end of said pendulum arm, a pivot mounting for horizontal alignment of said microscope interposed between said articulation and a microscope mounting, and a parallelogram-type control linkage including a chain drive for maintining said microscope in a given vertical orientation for any rotational position of said pendulum arm.

2. A microsurgical operating unit including a vertical support column mounted at its upper end at the ceiling of a room such as an operating theater, a sleeve rotatably supported on said vertical support column, a pivot arm for height adjustment, said pivot arm being rotatably mounted about a horizontal pivot axis disposed adjacent the free lower end of said sleeve, a vertical pendulum arm rotatably mounted at the free lower end of said pivot arm, a microscope mounted at an articulation on the free lower end of said pendulum arm, a pivot mounting for horizontal alignment of said miscroscope being interposed between said articulation and a microscope mounting, and a parallelogram-type control linkage including a chain drive for maintaining the microscope in a vertical orientation in any rotational position of said pendulum arm, with the pivot axes of said pivot arm, said pendulum arm pivot on said pivot arm, and said articulation pivot of said microscope on said pendulum arm all being arranged parallel to each other, with a first sprocket and said microscope mounting being rigidly secured to the articulation axis on the free lower end of said pendulum arm for alignment of said microscope in a vertical position during rotation of said pendulum arm, a second sprocket operatively coupled by a chain to said first lower sprocket, said second sprocket being rigidly secured to a shaft, said shaft being rotatably journalled in an upper articulation between said vertical pendulum arm and said pivct arm and operatively coupling said pivot arm to said pendulum arm, a lever secured to a projecting portion of said shaft, a connecting rod rotatively connected at its one end to the free end of said lever, and rotatably connected at its opposite end to a fixed pivot point on said sleeve rotatably mounted on said support column, said pendulum arm consisting of a hollow cylindrical member, said chain extending along the interior of said hollow cylindrical pendulum arm whereby said lever, said connecting rod and said chain form part of said parallelogram-type control linkage for said microscope.

3. A microsurgical operating unit as defined in claim 2, wherein a mass balance is provided for said pendulum arm and said microscope, for ease of handling of said microscope.

4. A microsurgical operating unit as defined in claim 3, wherein said pendulum arm is provided with an upper extension, and a counterweight is mounted on said upper extension.

5. A microsurgical operating unit as defined in claim 4, wherein said counterweight is mounted by a shaft on the pivot axis for said pivot arm, and a parallelogram rod connects the counterweight with a lever, the lever being secured to the lower pivot axis on said pendulum arm.

6. A microsurgical operating unit as defined in claim 1, wherein said pivot arm is coupled to a motor drive for height adjustments of said microscope, and a control panel for controlling said motor drive is arranged on said microscope mounting.

7. A microsurgical operating unit as defined in claim 6, wherein said shaft in the pivot axis of said pivot arm is provided with a counterweight, and said articulation for said pendulum arm in said pivot arm is continuously biased by spring assemblies of clamping devices.

8. A microsurgical operating unit as defined in claim 7, wherein said support column is provided with a mounting for a vertically adjustable lamp.

* * * * *